United States Patent
Haddadi et al.

(10) Patent No.: US 9,703,122 B2
(45) Date of Patent: Jul. 11, 2017

(54) METHOD FOR DETERMINING AT LEAST ONE VALUE OF A PARAMETER FOR CUSTOMISING A VISUAL COMPENSATION DEVICE

(71) Applicant: ESSILOR INTERNATIONAL (COMPAGNIE GENERALE D'OPTIQUE), Charenton-le-Pont (FR)

(72) Inventors: Ahmed Haddadi, Charenton-le-Pont (FR); Marie-Anne Berthezene, Charenton-le-Pont (FR); Isabelle Poulain, Charenton-le-Pont (FR); Cecile Petignaud, Charenton-le-Pont (FR); Loic Levraud, Charenton-le-Pont (FR); Sebastien Gayat, Charenton-le-Pont (FR); Fabien Divo, Charenton-le-Pont (FR); Benjamin Rousseau, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days.

(21) Appl. No.: 14/896,408

(22) PCT Filed: Jun. 3, 2014

(86) PCT No.: PCT/FR2014/051309
§ 371 (c)(1),
(2) Date: Dec. 7, 2015

(87) PCT Pub. No.: WO2014/195623
PCT Pub. Date: Dec. 11, 2014

(65) Prior Publication Data
US 2016/0124249 A1    May 5, 2016

(30) Foreign Application Priority Data

Jun. 7, 2013   (FR) ..................... 13 01309

(51) Int. Cl.
*A61B 3/10*   (2006.01)
*A61B 3/14*   (2006.01)
(Continued)

(52) U.S. Cl.
CPC .......... *G02C 13/005* (2013.01); *A61B 3/0025* (2013.01); *A61B 3/0033* (2013.01);
(Continued)

(58) Field of Classification Search
USPC ................................. 351/200–246
See application file for complete search history.

(56) References Cited

U.S. PATENT DOCUMENTS 8,959,781 B2   2/2015  Delort
9,116,365 B2   8/2015  Haddadi et al.
(Continued)

FOREIGN PATENT DOCUMENTS

AU   2010 249 222 A1   6/2012
DE   10 2011 009 646 A1   8/2012
(Continued)

OTHER PUBLICATIONS

International Search Report, dated Aug. 12, 2014, from corresponding PCT application.

*Primary Examiner* — Mohammed Hasan
(74) *Attorney, Agent, or Firm* — Young & Thompson

(57) ABSTRACT

A method for determining at least one value of a customization parameter for a visual compensation device includes the following steps: a) a user (1) equipped with an electronic terminal (2) captures at least one image or video sequence; b) telecommunicating the at least one image to a remote-support center (22); c) processing the at least one image in order to derive therefrom an instruction to correct or validate the captured image or video sequence; d) telecommunicating the correction or validation instruction from the remote- (Continued)

Figure 1:
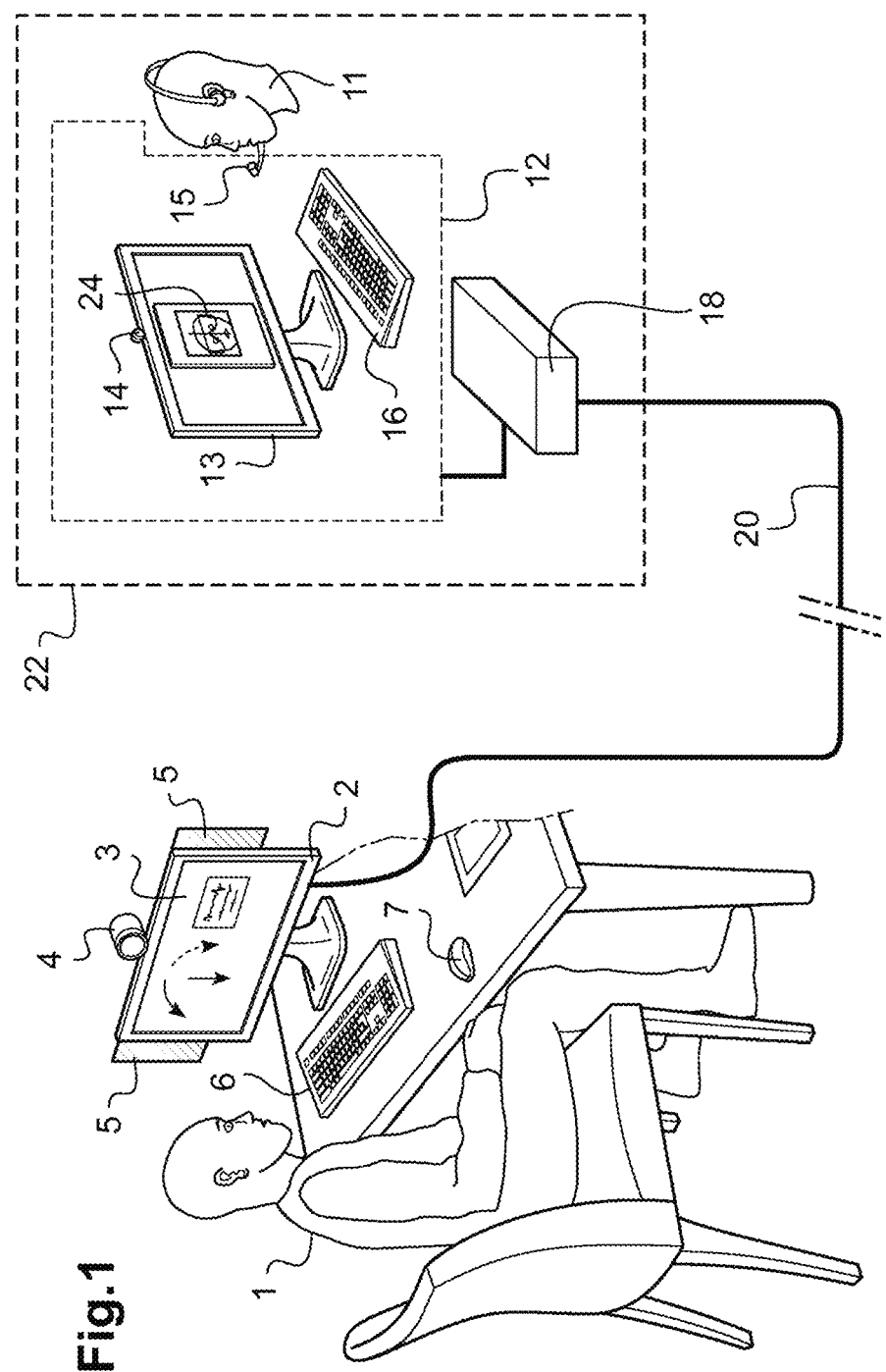

assistance center (22) to the terminal (2) of the user (1); e) displaying or emitting an audio or video message using the terminal; f) repeating the preceding steps until a validated image or video sequence is obtained; g) determining a value of the at least one customization parameter.

20 Claims, 3 Drawing Sheets

(51) Int. Cl.
    *G02C 13/00*     (2006.01)
    *A61B 3/11*     (2006.01)
    *A61B 3/113*     (2006.01)
    *A61B 3/00*     (2006.01)

(52) U.S. Cl.
    CPC .......... *A61B 3/0041* (2013.01); *A61B 3/0091* (2013.01); *A61B 3/111* (2013.01); *A61B 3/113* (2013.01); *A61B 3/145* (2013.01); *G02C 13/003* (2013.01)

(56) References Cited

U.S. PATENT DOCUMENTS

| | | | |
|---|---|---|---|
| 2003/0223037 A1* | 12/2003 | Chernyak | A61B 3/1015 351/209 |
| 2004/0189935 A1* | 9/2004 | Warden | G02C 7/027 351/204 |
| 2011/0273669 A1* | 11/2011 | Abitbol | A61B 3/1015 351/212 |

FOREIGN PATENT DOCUMENTS

| | | |
|---|---|---|
| FR | 2 971 861 A1 | 8/2012 |
| WO | 2011/067478 A2 | 6/2011 |

* cited by examiner

METHOD FOR DETERMINING AT LEAST ONE VALUE OF A PARAMETER FOR CUSTOMISING A VISUAL COMPENSATION DEVICE

TECHNICAL FIELD OF THE INVENTION

The present invention generally relates to the field of optometry.

It more particularly relates to an optometric method for determining the value of at least one personalization parameter of a piece of vision-correcting equipment for a user. In the present document, the expression "piece of vision-correcting equipment" is typically understood to mean a pair of vision-correcting spectacles comprising a spectacle frame and at least one mono- or multi-focal lens. Optometric measurements aiming to determine one or more personalization parameters are required to design and manufacture the refractive faces of corrective lenses and to adapt these lenses to the frame chosen by the user, depending on expected use conditions (near-vision, far-vision and/or vision during a specific activity).

PRIOR ART

Conventional optometric methods are known in which an optometrist uses one or more optometric appliances dedicated to the acquisition of precise measurements to take, in the presence of a user, measurements of parameters that allow a piece of vision-correcting equipment to be personalized. More particularly, conventional optometric methods aim to determine personalization parameters in order to allow the fit of corrective lenses in a particular frame to be tailored to an individual. Personalization parameters especially comprise parameters relating to the morphology of an individual, such as his interpupillary distance, the shape of the face of the individual, posture parameters such as head angle (roll, pitch and yaw) relative to a vertical line in a given posture, dynamic behavioral parameters characterizing the passage from one vision posture to another and also geometrical or physiological parameters relating to the face of the wearer and to a particular spectacle frame, such as a parameter characterizing the centration or position of a corrective lens in a spectacle frame relative to the optical center of rotation of an eye, the height of the eyes relative to the lower edge of the frame, the vertex (distance between the eye and the internal face of the spectacle lens), the face form angle of the frame or even the pantoscopic angle. The pantoscopic angle of a lens is defined as being the angle between the plane in which the corrective lens is held in the frame and a vertical plane, in a natural vision posture of the individual.

Certain personalization parameters relating to the morphology of an individual are generally measured whilst the individual is not wearing spectacles, whereas other personalization parameters are determined while the individual is wearing a spectacle frame or finished corrective spectacles in order to allow adjustment on the face of the individual after manufacture.

Conventional optometric methods generally involve interactions, lasting a limited length of time, between an optometrist, a user, one or more optometric appliances and a piece of corrective equipment, these interactions allowing the characteristics of a piece of vision-correcting equipment perfectly adapted to the morphology and vision-correction requirements of the user to be defined.

These optometric methods are complex and require the user to visit an optometrist and specific optometric appliances. In addition, it is not possible to take certain measurements in a length of time limited to a few tens of minutes. In particular, conventional optometric methods generally do not take into account movement-related behaviors of the user, such as the combined movement of the head and gaze used to pass from a far-vision posture to a near-vision posture. These conventional methods do not incorporate vision measurements taken while the user is moving, for example in order to take into account vision positions intermediate between the far-vision and near-vision positions.

For a number of years, it has been possible to buy spectacles online. The supplier offers to the user a range of spectacle frames, which frames are associated with a choice of lenses defined depending on a vision-correction prescription established beforehand by a specialist in ophthalmology. A simplified method for determining a personalization parameter by means of a camera of a desktop, laptop or tablet computer and a piece of image-processing software is also offered. This method makes it possible for a user to evaluate a personalization parameter using his desktop, laptop or tablet computer, without having to visit an optometrist. The personalization of this type of spectacles is generally limited to the approximate estimation of a small number of parameters such as interpupillary distance. Thus, document WO 2011/067478 (JMC Delort) describes a method and device for taking measurements with regard to producing a pair of corrective spectacles, there being no direct physical contact between the wearer and the professional who prepares the spectacles. This method is based on measurements and photographs taken by the client whilst he is equipped with a measuring device, and on the transmission of these photographs and measurements to a remote location.

However, the quality of the vision-correcting spectacles thus obtained is generally much lower than that of spectacles defined and adjusted using a conventional optometric method. In particular, miscentering of the lenses and interpupillary distance errors are observed. These shortcomings are in particular due to mismeasurement of personalization parameters. On the one hand, the user does not have at his disposal means for checking his position relative to the camera: the distance between the camera and the individual is unknown, and hence it is necessary to scale the image. On the other hand, the cameras of desktop, laptop or tablet computers generally distort images substantially. Thus, a personalization parameter of a pair of vision-compensating spectacles determined by means of an integrated camera cannot generally be relied upon. These shortcomings may lead to unsatisfactory correction of the vision of the user and/or visual discomfort. In addition, the user is required, in certain cases, to fixate on the camera in a precise way (in order to obtain precise measurements, such as precise measurements of monocular pupillary distance, the height of the eye, etc.). However, it is difficult for the user to position himself correctly, without help, because he is not able to simultaneously observe the camera and instructions displayed on the screen. Specifically, if he looks at the screen, he modifies his posture with respect to the camera. The quality of the measurements is thus affected by positional errors.

Lastly, the camera and the screen of a desktop computer, a laptop computer, a tablet computer or a cellphone are generally integral components of the device, thereby complicating measurement of certain parameters, for example pantoscopic angle from a view of the profile of a user, since in this posture the screen is outside of the field of view of the user.

There is a need for a method for determining at least one personalization parameter of a piece of vision-correcting equipment, this method being implementable remotely, for example in the home of a user, and this method providing reliable measurements of at least one personalization parameter.

There is a need for a method for determining at least one personalization parameter of a piece of vision-correcting equipment, this method taking a plurality of tens of minutes, or even a plurality of hours, to implement and allowing certain personalization parameters, which cannot be measured in a time limited to one or a few tens of minutes, to be taken into account, without extra expense on the part of the user. It is desirable for example to average pupillary distance measurements, height measurements, etc., originating from a plurality of sequences of acquisitions spread over time in order to improve the precision of the measurements.

SUBJECT OF THE INVENTION

In order to remedy the aforementioned drawback of the prior art, the present invention provides an optometric method in which measurements are carried out from an image-capturing terminal and validated remotely after having been checked.

More particularly, according to the invention a method is provided for determining at least one value of a personalization parameter of a piece of vision-correcting equipment for a user, employing an electronic terminal comprising a graphical interface, an image capturing apparatus comprising an image sensor, and audiovisual communication means, the method comprising the following steps:

a) capturing at least one image or video sequence of the user by means of the image capturing apparatus;

b) communicating said at least one image or video sequence captured in step a) to a remote-assistance center located remotely from the electronic terminal, the remote-assistance center comprising at least one checking terminal;

c) checking processing, by the remote-assistance center, of said at least one image or video sequence transmitted in step b), in order to deduce therefrom, on account of a position, a posture or a sequence of movements of the user in front of the image capturing apparatus, a captured image or video sequence correction or validation instruction;

d) communicating from the remote-assistance center to the electronic terminal of the user said correction or validation instruction;

e) the electronic terminal displaying or emitting a video or audio message informing the user of the validation of the image or video sequence capture or requesting the user to position or move himself relative to the image capturing apparatus in accordance with the correction instruction;

f) reiterating the preceding steps until a validated image or video sequence is obtained; and g) determining at least one value of said personalization parameter depending on said captured and validated at least one image or video sequence.

The method of the invention allows an image captured remotely by means of a terminal to be validated and a value of at least one personalization parameter of a piece of vision-correcting equipment to be determined.

Thus, the method avoids the use of specific and expensive optometric appliances that require the user to visit a place where such optometric appliances can be found. Nevertheless, the method makes it possible to obtain personalization parameter values checked by a competent person who helps the user take the measurements remotely.

Advantageously, said at least one personalization parameter comprises one of the following parameters:

an interpupillary distance or left or right monocular pupillary distance parameter;

a user face shape parameter;

a user posture parameter;

a dynamic behavioral movement-related parameter of the user;

a centration parameter of a corrective lens in a spectacle frame;

a parameter characterizing the position of the pupillary centers or CRE of the eyes in a frame of reference associated with the frame;

a vertex parameter, for example a lens-eye distance;

a parameter characterizing the position or inclination of the frame or of the piece of equipment or of the lens in a face or environment frame of reference, for example a face form angle or a pantoscopic angle; and adjustment parameters of the frame in a face frame of reference.

More precisely, one or more face shape parameters may make it possible to determine the general shape of the face from a set of predefined shapes such as: square, round, rectangular, oval, etc. and/or adjustment parameters of a spectacle frame to be determined. A user posture parameter make it possible to determine a posture from a predefined set of postures such as: an upright far-vision posture, a near-vision reading posture, a posture adopted when working on a computer. A movement-related behavioral parameter of the user represents a parameter from one of a set of predefined movements such as: a movement from a first posture to another posture, a nodding movement of the head from front to back, a pivotal movement of the head about a vertical axis, etc. A centration parameter allows a parameter characterizing the position of a lens relative to a spectacle frame to be determined (in particular including a parameter characterizing the position of a lens relative to a frame).

The following are other nonlimiting and advantageous features of the method according to the invention:

in step d), the remote-assistance center delivers a validation instruction if said at least one image or video sequence is good enough to at least contribute to determining the value of the sought personalization parameter, or delivers a correction instruction in the contrary case, respectively;

in step d), the remote-assistance center delivers a correction instruction to correct a centration position of the eyes in front of the image capturing apparatus, a posture of the user, a sequence of movements of the user relative to the image sensor of the image capturing apparatus, or compliance with a protocol presented by the terminal and to be executed by the wearer in order to obtain a validated image;

during the reiteration of steps a) to e), the correction instructions delivered by the remote-assistance center are such that the messages delivered to the user lead him to adopt a series of ocular fixations or ocular pursuits and/or a series of postures in which the Frankfurt plane and/or sagittal plane of the user are oriented at a predefined angle to the optical axis of the image capturing apparatus, or to comply with and execute a protocol presented by the terminal in order to obtain a validated image; and step a) comprises the image capturing apparatus taking a video recording of a video sequence of the user in the remotely validated series of postures;

the series of postures of the user in front of the image capturing apparatus is such that the Frankfurt plane and the sagittal plane of the user make to the optical axis of the image capturing apparatus an angle smaller than a predefined threshold and in step g), an interpupillary distance or a monocular pupillary distance is calculated;

the series of fixations that the user makes in front of the image capturing apparatus is such that his gaze direction makes, to the direction of the object fixated, an angle smaller than a predefined threshold (optional); and in step d), the audio-video remote-assistance comprises communicating to the user rescaling instructions including capturing at least one image of an element of known size, preferably placed in proximity to the eyes of the user, for example a clip fastened to the frame, or capturing an image representative of the interpupillary distance of a user whose interpupillary distance is already known, or measuring a known reading distance in order to correct convergence, or even capturing an image of a frame having at least one predefined geometrical dimension.

Preferably, the user and a member of personnel of the remote-assistance center interface over a direct link. This direct link especially makes it possible to aid the user in particular, relatively complex, cases that are not easily automatable. This direct link furthermore makes it possible to provide a service to the client making it possible to reassure him that he is proceeding correctly and to validate the various steps.

Advantageously, step d) of audio-video remote-assistance comprises the following substeps:

a step in which the remote-assistance center transmits to the graphical interface of the terminal of the user a video stream or a known image; and a step of capturing an image of the face or at least one eye of the user in response to this video stream or this known image; and/or a step of checking whether this response of the face or at least one eye of the user to the transmission of said video stream or said known image by the remote-assistant center makes sense.

Advantageously:

step g) comprises verifying a value of a geometric adjustment parameter of a spectacle frame by comparing said determined value with a reference value;

step g) comprises measuring reading distance or gaze direction or by how much the head is lowered; and the messages emitted by the terminal in step e) comprise a request for the user to rotate his head about a horizontal axis and/or about a vertical axis and the processing of said at least one image or captured video sequence comprises detecting in the image a notable point of the ear of the user such as the tragion.

In one particular embodiment, in step a) during the capture of at least one image or video sequence, the user is equipped with a spectacle frame;

the messages emitted by the terminal allow the user to be guided into at least one first posture in which the sagittal plane is aligned with the axis of the image capturing apparatus and at least one second posture in which the sagittal plane makes a nonzero angle to the axis of the image capturing apparatus; and the images or video sequences are validated in these two postures.

Advantageously, the method comprises an additional step of selecting a language for the user from a plurality of languages, and, a set of validation and user guidance messages being recorded, each message is informationally tied to its audiovisual implementation in each of the languages of the plurality of languages, the message being delivered by the terminal to the user in correspondence with the instruction delivered by the remote-assistance center and in the language selected by the user.

Advantageously, step c) of processing, by the remote-assistance center (22), of said at least one image or video sequence transmitted in step b) and/or step d) of communicating, from the remote-assistance center (22) to the electronic terminal (2) of the user, said correction or validation instruction, is carried out by an automated system or by an optician possessing a digital signature.

DETAILED DESCRIPTION OF ONE EXAMPLE EMBODIMENT

The following description, given with regard to the appended drawings and by way of nonlimiting example, will allow the invention and how it may be implemented to be better understood.

Figure 2:
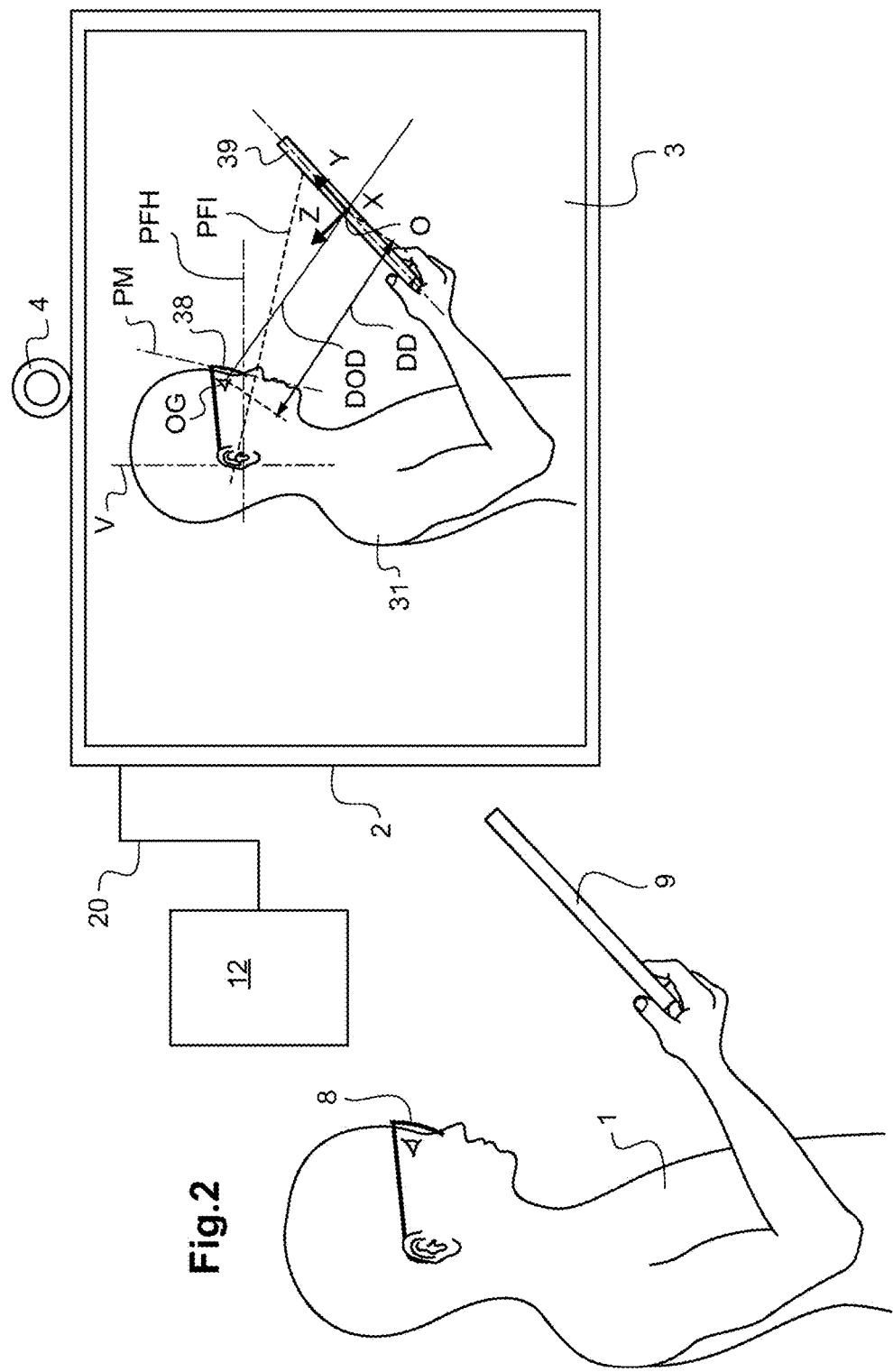
Figure 3:
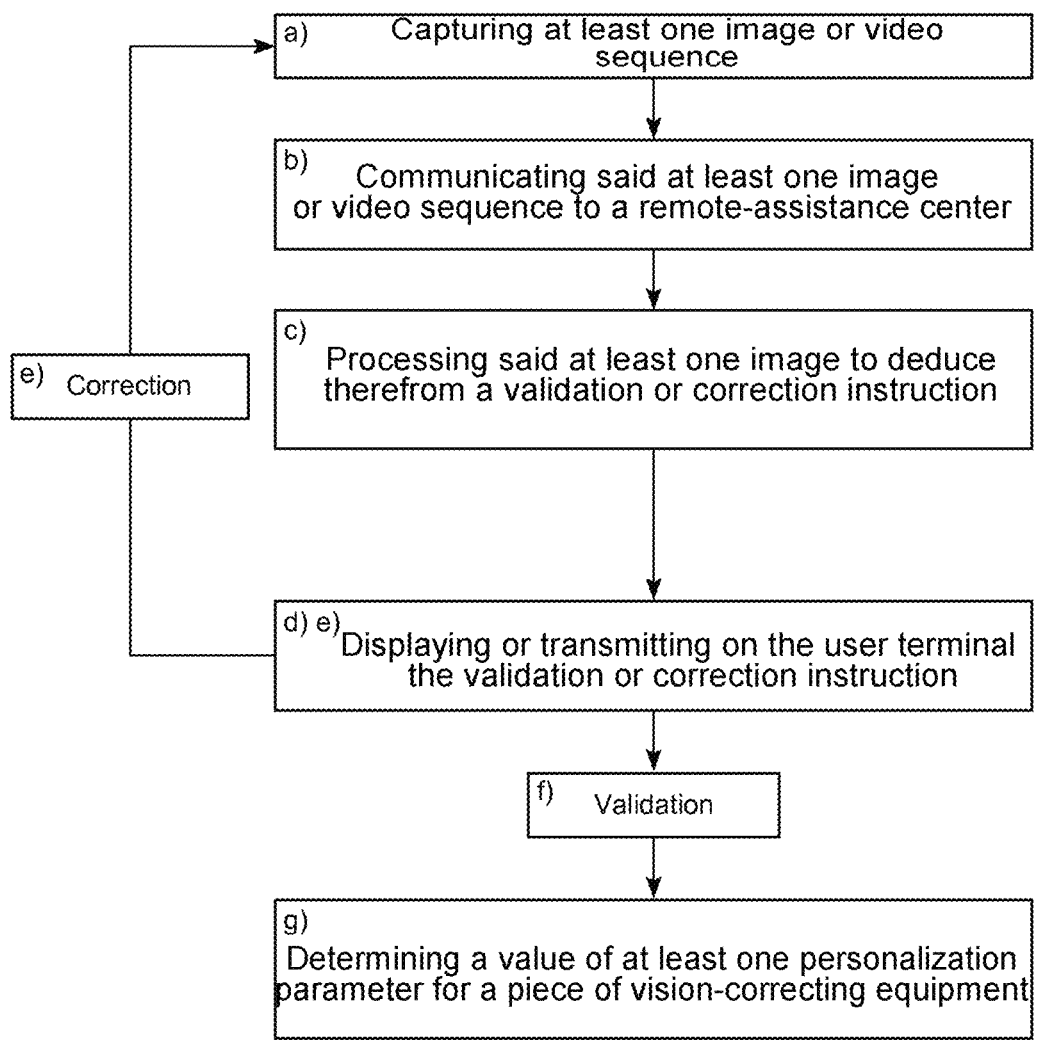

In the appended drawings:

FIG. 1 schematically shows an exemplary implementation of the method of the invention;

FIG. 2 is a profile view of the individual holding in his hand an object in a near-vision posture and of a terminal according to another exemplary implementation of the invention; and FIG. 3 shows a chart of the steps of a method according to one embodiment of the invention.

Device

FIG. 1 schematically shows the elements of a device employed to determine or measure at least one value of a personalization parameter of a piece of vision-correcting equipment intended for an individual 1 or user.

The device comprises, on the one hand, an audiovisual terminal 2 and, on the other hand, a checking terminal 12, which are located remotely from each other and connected to an information processing system 18 by telecommunications means 20 such as the Internet or another type of network.

The audiovisual terminal 2 of the user comprises a viewing screen 3, a camera 4, and an audio periphery such as a set of loudspeakers 5 or headphones. The audiovisual terminal 2 may consist of a desktop or laptop computer equipped with interfacing means such as a computer keyboard 6 or a mouse 7, or a tablet computer comprising a touch screen and/or voice control.

The checking terminal 12 comprises a viewing screen 13 and interfacing means such as a computer keyboard 16 or a microphone 15. The checking terminal 12 may comprise the interface of the information processing system 18.

Advantageously, the checking terminal 12 is located in a remote-assistance center 22, where a competent person 11 is able to interact with the various interfaces of the checking terminal. The expression "remote-assistance center" is understood to mean an assembly of technical means and human resources comprising at least one checking terminal 12 and one person 11 who is competent to use this checking terminal 12.

The remote-assistance center 22 may comprise one or more checking terminals. One competent person 11 may operate one or more checking terminals 12. A plurality of checking terminals 12 may be connected to the same information processing system 18. A plurality of people 11 who are competent to operate a plurality of checking terminals 12 may work at one remote-assistance center 22.

FIG. 2 shows another exemplary embodiment of an audiovisual terminal 2 and a checking terminal 12, which are connected to an information processing system 18 by telecommunications means 20.

Method

The individual 1 at least one personalization parameter of which it is being sought to determine, is installed in front of an electronic audiovisual terminal 2. Advantageously, the individual 1 is placed in his habitual environment. Alternatively, the audiovisual terminal 2 may be located at a point of sale of a chain of opticians and connected to the checking terminal 12 via a dedicated telecommunications network 20.

Alternatively, the electronic audiovisual terminal 2 and the checking terminal 12 are integrated into one and the same housing, such as a photo booth. In this case, the checking terminal 12 comprises entirely automated processing means for acquiring images and for communicating audiovisually with the individual 1. The individual 1 places himself in front of the camera 4 of the audiovisual terminal 2. By way of illustrative example, it is desired to measure the interpupillary distance of the individual. The expression "interpupillary distance" (IPD) is understood to mean the distance between the centers of the pupils of the two eyes and the expression "monocular pupillary distance" (½-IDP) is understood to mean the distance between the center of the pupil of one eye and the nose or sagittal plane.

The individual 1 executes a software program intended to acquire at least one image or one video sequence by means of the camera 4.

Initiation of the software program may comprise an optional first step of selecting a language for the user from a plurality of languages so that the audiovisual messages emitted by the terminal are expressed in the language selected by the user.

A person 11 competent to check the acquisition of the measurement data is stationed in proximity to the checking terminal 12. Preferably, the competent person 11 is a person qualified in optometry or an optician who is qualified to evaluate the quality of the images captured with a view to obtaining an optometric measurement. Even more preferably, the competent person 11 is qualified to append a signature or a seal of certification so as to officially validate the personalization parameter values determined by the measuring method. The language used by the checking terminal 12 is not necessarily the same language as the language selected by the user, the information processing system 18 being configured to enable communication between the audiovisual terminal 2 and the checking terminal 12 in a plurality of languages (for the checking terminal and for the electronic terminal of the user, respectively).

The checking terminal makes it possible for the competent person 11 for example to view an image 24 or a video sequence captured by the camera 4 of the audiovisual terminal 2. The information processing system 18 comprises digital processing means allowing at least one value of a personalization parameter to be extracted from an image or an image sequence validated by the competent person 11.

The competent person 11 may interact with the user 1 by inputting one or more instructions into the checking terminal 12, in order to trigger remotely the emission of audio and/or visual messages from the audiovisual terminal 2.

A database is loaded into the information processing system 18 or locally in the form of a "plug-in" into the electronic terminal 2. This database comprises a series of control instructions, each control instruction being associated informationally with a message intended to be represented on the terminal 2. Particularly advantageously, each message is informationally tied to its audiovisual implementation in each of the languages of the plurality of languages offered to the user, the message being delivered by the terminal 2 to the user 1 in correspondence with the instruction delivered by the remote-assistance center and in the language selected by the user 1. Analogously, each instruction of the series of control instructions is informationally tied to its translation and its implementation in each of the languages of the plurality of languages available to the checking terminal 12.

For example, the competent person inputs a validation instruction via a button displayed on the screen 13 of the checking terminal 12 and thereby triggers the display of a visual message, for example OK, on the screen 3 of the terminal 2 of the user. In another example, a non-validation instruction triggers the emission of an audio alarm signal message and the display of a visual message on the screen 3, for example taking the form of a video stream displaying the image of a flashing arrow accompanied by a short text in the language selected by the user, the textual message for example requesting the user to incline his head in the direction indicated by the flashing arrow.

The database thus ensures the informational and linguistic correspondence between an instruction input by the competent person and a message or a series of messages emitted by the terminal of the user. The database thus automatically translates the emitted or displayed message into the language of the user.

Provision is also made for communication in the inverse direction i.e. From the user 1 to the remote-assistance center 22. For this purpose, the database comprises a series of user control instructions, each user control instruction being associated informationally with a message intended to be represented on the checking terminal 12 of the remote-assistance center 22. Preferably, each user control instruction is informationally tied to its implementation in each of the languages of the plurality of languages available to the checking terminal 12.

For example, the user may input an instruction or a question into his terminal that triggers the translation of this instruction or question and the transmission of a message to the checking terminal 12 of the competent person. For example, the user may press on a button "?" that triggers the display of a message "request for assistance" on the checking terminal 12, translated into the language available to the competent person.

By way of illustrative example, it is desired to measure an interpupillary distance parameter of the individual. The individual 1 launches an image acquiring program. A first captured image is transmitted via the telecommunications means 20 to the remote-assistance center 22 or remote processing center. On the screen 13 of the checking terminal 12 the captured image 24 and at least one indicator for evaluating the quality of this image are displayed. The quality indicator may be calculated by the information processing system 18 or be evaluated and input by the competent person 11.

The competent person 11 is responsible for evaluating the quality of the captured image and validating or not this image for an interpupillary distance measurement. The method does not necessarily rely on one or more quality criteria pre-recorded in the information processing system 18 but may also rely on a subjective evaluation of the quality of the captured image by the competent person 11, depending on his competences and his know-how.

By way of example, let us assume that the first image is not suitable for an interpupillary distance measurement, for reasons of misframing of the image or incorrect inclination of the head of the individual.

The competent person 11 inputs, for example via the keyboard 16 or another periphery of the checking terminal 12, an instruction indicating non-validation of the first captured image.

Automatically, or on a command from the remotely located competent person 11, the information processing system 18 processes this non-validation instruction. More precisely, the informational system points to the "message" field of the database corresponding to the non-validation instruction in the language of the user. The information processing system 18 triggers delivery to the terminal 2 of an audiovisual message corresponding to the non-validation instruction, the message delivered for example being an audio message delivered by the loudspeakers 5 and/or a visual message displayed on the viewing screen 3. The terminal 2 displays a visual message and/or emits an audio message requesting the user to position or move himself in accordance with the correction instruction. Advantageously, the competent person may guide the user 1 to modify his posture in front of the camera. The visual messages may comprise textual messages, icons or pre-recorded video messages. Following the repositioning of the user, the camera 4 captures a second image or a second video sequence.

The second captured image is transmitted via the telecommunications means 20 to the remote-assistance center 22.

The second captured image and the indicator for evaluating the quality of this image are displayed on the checking terminal 13. If the quality indicator meets quality criteria, the competent person 11 may validate the second image. The input of a validation command by the competent person 11 is recorded in the information processing system 18. The information processing system 18 points to the field of the database corresponding to the validation instruction in the language of the user and triggers transmission of a validation message to the terminal 2 of the user.

The terminal 2 displays a visual message and/or emits an audio message informing the user 1 of the validation of the image or video sequence capture.

In the case where the second captured image does not meet the quality criteria, the information processing system 18 once again delivers a message indicating non-validation of the second captured image, and the image capturing method is reiterated or abandoned by the user.

The information processing system 18 processes the captured and validated video sequence or image digitally in order to extract therefrom the value of the sought personalization parameter.

In one example in which the shape of the face of the user is determined, an image is processed in order to locate the outline of the face in the image and, for example, to associate therewith a predefined geometric shape.

In the case of a measurement, such as an interpupillary distance measurement, based on an image taken with the camera, this measurement assumes that the scale of the image is known or can be determined. The dimensions of the image depend on the optical properties of the image sensor of the camera 4, but also on the distance between the camera and the individual.

Advantageously, the method comprises an additional scaling step. This scaling may be carried out by capturing an image of the face of the user with an object of known size placed in the field of the image, preferably in the same image plane as the face of the individual. For example, the competent person may request, via the interface of the terminal 2, the user to place a graduated ruler or a test pattern size on his forehead. Alternatively, if the user has at his disposal a spectacle frame having at least one predefined geometrical dimension, the scaling step may comprise a step of capturing an image of the spectacle frame featuring this predefined geometrical dimension. The information processing system 18 processes the image of the test pattern or object of known size in order to deduce therefrom a scaling factor of the camera for a given working distance.

Advantageously, the image processing applied to an image or a captured video sequence comprises detecting in the image a notable point of the ear of the user such as the tragion. The aim of this image processing is for example to determine a measurement posture in which the axis of the camera is located in the Frankfurt plane of the user, the Frankfurt plane being as is known per se the anatomical plane defined by the inferior orbital margins of the eyes and the tragions. In practice, the competent person 11 verifies that the lower orbital margin of each eye and the tragions are aligned with the pupil of the camera, which amounts to saying that they are located at the same height in the image. One protocol consists for example in the competent person 11 requesting the user 1 to capture a first front-on image, and then for the user 1 to tilt his head upwards or downwards until the Frankfurt plane is aligned parallel to the axis of the camera. This alignment may optionally be followed by a rotation of the head of the user 1 to the right or left in order to allow the competent person 11 to better see the tragions and thus refine the posture of the user 1. Specifically, the tragions are generally not visible in the front-on image but the consultant may estimate their position from that of the ears. This measurement posture makes it possible to obtain a measurement of the height of the eyes relative to the lower edge of the frame, almost equivalently to a conventional measurement in an orthostatic posture with a camera level with the eyes. This measurement posture especially makes it possible to avoid postures in which the measurements, for example of height, would be completely corrupted by an excessive angle between the axis of the camera and the Frankfurt plane. This may be applied without a frame, for example for the virtual try-on of frames, image processing allowing the heights thereof to be deduced from a virtual fit between a representation of the frame and an image of the face of the user. Such a frameless measurement is certainly approximate but nevertheless allows important sources of errors to be eliminated. Alternatively, the measurement may be carried out with an actual frame for results of higher quality.

Advantageously, the competent person 11 of the remote-assistance center may guide the user into various measurement postures depending on the tests and measurements to be carried out.

Analogously, it is also possible to determine a posture of the user in which the sagittal plane is parallel to the axis of the camera.

Particularly advantageously, one measurement posture corresponds to a posture in which the sagittal plane and the Frankfurt plane of the user are aligned with the axis of the camera.

By way of nonlimiting example, mention may be made, apart from the posture for measuring height detailed above, of a general posture, a posture for measuring monocular pupillary distances, a posture or a series of movements for determining eye-lens distance (ELD) or even for measuring the pantoscopic angle of a pair of spectacles in a given vision posture.

General Posture:

The competent person 11 or a consultant of the remote-assistance center or an automate verifies in step c) that the wearer is a distance from the screen larger than a threshold, for example by asking him to hold his arm out toward the screen in such a way that he only just touches it, or for example by checking that the face of the user 1 occupies a minimal space in the image. The competent person 11 also verifies, if a scaling element is present, that it is correctly positioned and/or that the head of the user 1 is not inclined so as to make a pitch angle larger than a preset threshold. Lastly, the consultant 11 verifies that the user 1 is indeed looking at the camera 4, for example by asking him to point to the camera with his index finger. The scaling instructions for example comprise checking the position of the wearer relative to the camera and/or whether the scaling element (clip, frame or other element of known size) is present and correctly positioned.

Posture for the Measurement of Monocular Pupillary Distance:

The consultant 11 triggers the transmission of a video sequence that makes it possible to determine whether or not the posture, and more precisely the angle of inclination of the head (head cape), of the wearer is suitable for correctly measuring monocular pupillary distance, for example by verifying that the face of the user 1 is indeed positioned facing the camera 4. This measuring step may be automated using algorithms allowing this angle of inclination of the head (head cape) to be estimated (for example using the device Seeing Machine). The competent person 11 validates the measurement posture either when the instructions transmitted to the user 1 have allowed a zero angle of inclination (zero head cape) to be obtained, or when the angle of inclination is smaller than a predefined threshold.

Posture for Determining Eye-Lens Distance (ELD):

This posture is illustrated for example in FIG. 2, in which the processing system is either a remote-assistance center with a competent person 11 or an entirely automated system.

The individual 1 wears a spectacle frame 8 equipped with lenses. By way of nonlimiting example, a spectacle frame 8 worn by the user 1 during a measurement may be an old spectacle frame or a newly received piece of vision-correcting equipment in order to check, for example, the pantoscopic angle.

The competent person 11 asks the user 1 to look at the camera 4 and to turn his head, analogously to the movements made in front of an Essilor Visioffice appliance, and then in step c), the competent person 11 ensures that the rotation of the head is sufficient to allow this parameter to be measured.

In the case of an automated system, an image acquisition and processing program launches following the input of a command via the audiovisual interface by the individual. The camera 8 initiates acquisition of an image or preferably a sequence of images. During this acquisition, the individual makes a pivoting movement of the head from left to right over an amplitude of about ±5 degrees, so that at least one image of the sequence of images corresponds to a profile view of the user. The image processing system processes the image(s), for example in real-time, in order to analyze the posture of the user: the processing system selects an image corresponding to a profile view 31 of the user. Particularly advantageously, the automatic processing system emits audiovisual messages in order to guide the individual, so that he is a sufficient distance to be in the field of view of the camera and so that he modifies his cephalic posture i.e. the inclination of the head from left to right and/or front to back.

Thus, the user is guided by the processing system so that the latter validates that the acquired image 31 effectively corresponds to a profile view, for example to within better than ±5 degrees, and not to a three-quarter view for example.

The camera 4 optionally has a zoom suitable for capturing a profile image of the individual comprising his head and one arm in order to allow the posture of the individual to be analyzed, for example his near-vision posture, when the individual is holding an object 9, such as a book or a tablet computer, in his hand.

Advantageously, as illustrated in FIG. 2, the system comprises facial recognition means that make it possible to determine the position of the head of the individual in the acquired image, and of certain particular points, such as the position of the right eye OD or left eye OG, and to detect the position of the outline of the spectacles.

The image processing system is also configured to detect the image 39 of an object used as a target for intermediate-vision or near-vision gaze and the position of a frame of reference (OX, OY, OZ) associated with this object 9.

From the identification of these particular points in the image, the processing system is for example configured to automatically determine in the image 31 the positions and orientations of an inclined Frankfurt anatomical plane PFI under the visual conditions of the image capture, for example near- or intermediate-vision conditions, or of a horizontal Frankfurt anatomical plane PFH under far-vision conditions.

As is known per se, the processing system is able to compensate for parallax errors in the image 31.

Thus, a cephalic posture parameter, such as a distance DD, DG between the head or one of the eyes OD, OG of the individual and the object 9 and, for example, more precisely the distance DD, DG between the center of rotation of the eyes OD, OG of the individual and the object 9, is also measured.

The distance measurement is calibrated using known methods, for example via the acquisition of an image of an object of known size, such as a graduated ruler or a credit card.

Provision may also be made to determine one of the following geometric parameters: a lens holding plane PM; and a straight observation line DOD, DOG connecting one of the eyes OD, OG of the individual to a particular point O of the object 9.

Thus, provision may also be made to measure at least one of the following parameters: a pantoscopic angle between the holding plane PM, in the image, of a lens 38 of the spectacles and a vertical line V in an identified vision posture. For the measurement of certain personalization parameters, the user 1 does not wear a piece of vision-correcting equipment or a demonstration frame. For other personalization parameter measurements (centration of the lenses relative to a particular frame for example), or to check the fit of the spectacles after manufacture, it is necessary for the user to be wearing the spectacles during the capture of the image or video sequence.

The audiovisual messages on the terminal 2 may comprise messages requesting the user to put on the spectacles 8 or take off the spectacles 8, or to put on a demonstration frame devoid of corrective lenses. For measurements of certain vision postures, for example a near-vision reading posture, an audiovisual message may invite the user to pick up an object 9 such as a book.

The remote-assistance checking step may comprise a step of verifying that the instruction to take off or put on a pair of spectacles or to put on a frame without corrective lenses has been executed.

In comparison to conventional optometric measurements carried out with optometric appliances by a specialist, the remote-assistance method allows measurements that take much longer to be taken and a measurement that is an average of a series of measurements to the obtained without additional cost.

The length of time that the user would like to spend on the measurements may thus be defined and input by the user at the start of the method or recorded by the remote-consultant. Depending on this length of time, a choice of personalization measurements to be carried out may be offered or defined on initiation of the method. The choice of personalization measurements to be carried out may also be defined depending on a detected or indicated lifestyle (such as a person who works with computers, alternated reading and far vision, etc.). Another advantage of the method is that it makes it possible to separate various measurements temporally i.e. to take the various measurements at different times of the day, in order to take into account variation in conditions or in the vision parameters of the user.

Advantageously, the competent person 11 is not required to intervene continuously throughout the duration of the method, especially before the image capturing step. Intervention by the competent person 11 is required during the step of validation or non-validation of an image or a sequence of images and optionally to guide a user to modify his posture with a view to a new acquisition.

It is possible for a given competent person 11 to check in parallel, from a given checking terminal 12, a plurality of users, each user being located in front of a separate terminal 11. In this case, the competent person 11 provides assistance in succession and intermittently to each of the users.

Intervention by the competent person 11 may also be required after the image processing by the information processing system, after the one or more sought personalization parameters have been determined, and at the end of the protocol for official validation and/or the digital signature of the personalization parameters determined by the information processing system. The remote-consultant thus plays the role of a "door-to-door" optician.

Advantageously, a database allows the personalization parameter values associated with a user and with defined measurement conditions to be recorded.

A chain of opticians or a manufacturer of vision-correcting lenses may then collect the results of these personalization parameter measurements, which have been validated by a competent person, in order to exploit them to start the manufacture of a piece of vision-correcting equipment meeting the requirements of the user. The personalization parameter values may for this purpose be complemented by other measurements, such as ophthalmological measurements of an individual, especially comprising the curvature, axis and cylinder values required to correct his vision.

The remote-assistance method makes it possible to determine at least one value of a personalization parameter in a checked pre-sale phase. This remote-assistance method saves the optician time.

The method may also be applied after a pair of correcting spectacles has been manufactured in order to check the fit of the spectacles for the user.

The invention claimed is:

1. A method for determining at least one value of a personalization parameter of a piece of vision-correcting equipment for a user, employing an electronic terminal comprising a graphical interface, an image capturing apparatus comprising an image sensor, and audiovisual communication means, the method comprising the following steps:
   a) capturing at least one image or video sequence of the user by means of the image capturing apparatus;
   b) communicating said at least one image or video sequence captured in step a) to a remote-assistance center located remotely from the electronic terminal, the remote-assistance center comprising at least one checking terminal;
   c) checking processing, by the remote-assistance center, of said at least one image or video sequence transmitted in step b), in order to deduce therefrom, on account of a position, a posture or a sequence of movements of the user in front of the image capturing apparatus, a captured image or video sequence correction or validation instruction;
   d) communicating from the remote-assistance center to the electronic terminal of the user said correction or validation instruction;
   e) the electronic terminal displaying or emitting a video or audio message informing the user of the validation of the image or video sequence capture or requesting the user to position or move himself relative to the image capturing apparatus in accordance with the correction instruction;
   f) reiterating the preceding steps until a validated image or video sequence is obtained; and
   g) determining at least one value of said personalization parameter depending on said captured and validated at least one image or video sequence.

2. The method as claimed in claim 1, in which said at least one personalization parameter comprises one of the following parameters:
   an interpupillary distance or left or right monocular pupillary distance parameter;
   a user face shape parameter;
   a user posture parameter;
   a dynamic behavioral parameter of the user;
   a centration parameter of a corrective lens in a spectacle frame;
   a parameter characterizing the position of the pupillary centers or CRE of the eyes in a frame of reference associated with the frame;
   a vertex parameter, for example a lens-eye distance;
   a parameter characterizing the position or inclination of the frame or of the piece of equipment or of the lens in a face or environment frame of reference, for example a face form angle or a pantoscopic angle; and
   adjustment parameters of the frame in a face frame of reference.

3. The method as claimed in claim 1, in which, in step d), the remote-assistance center delivers a validation instruction if said at least one image or video sequence is good enough to at least contribute to determining the value of the sought personalization parameter, or delivers a correction instruction in the contrary case, respectively.

4. The method as claimed in claim 1, in which in step d), the remote-assistance center delivers a correction instruction to correct a centration position of the eyes in front of the image capturing apparatus, a posture of the user, a sequence of movements of the user relative to the image sensor of the image capturing apparatus, or compliance with a protocol presented by the terminal and to be executed by the wearer in order to obtain a validated image.

5. The method as claimed in claim 1, in which:
during the reiteration of steps a) to e), the correction instructions delivered by the remote-assistance center are such that the messages delivered to the user lead him to adopt a series of ocular fixations or ocular pursuits and/or a series of postures in which the Frankfurt plane and/or sagittal plane of the user are oriented at a predefined angle to the optical axis of the image capturing apparatus, or to comply with and execute a protocol presented by the terminal in order to obtain a validated image; and
step a) comprises the image capturing apparatus taking a video recording of a video sequence of the user in the remotely validated series of postures.

6. The method as claimed in claim 5, in which the series of postures of the user in front of the image capturing apparatus is such that the Frankfurt plane and the sagittal plane of the user make to the optical axis of the image capturing apparatus an angle smaller than a predefined threshold and in which in step g), an interpupillary distance or a monocular pupillary distance is calculated.

7. The method as claimed in claim 1, in which in step d), the audio-video remote-assistance comprises communicating to the user rescaling instructions including capturing at least one image of an element of known size, preferably placed in proximity to the eyes of the user, or capturing an image representative of the interpupillary distance of a user whose interpupillary distance is already known, or measuring a known reading distance in order to correct convergence, or even capturing an image of a frame having at least one predefined geometrical dimension.

8. The method as claimed in claim 1, in which step d) of audio-video remote-assistance comprises the following sub-steps:
a step in which the remote-assistance center transmits to the graphical interface of the terminal of the user a video stream or a known image; and
a step of capturing an image of the face or at least one eye of the user in response to this video stream or this known image.

9. The method as claimed in claim 1, in which step g) comprises verifying a value of a geometric adjustment parameter of a spectacle frame by comparing said determined value with a reference value.

10. The method as claimed in claim 1, in which step g) comprises measuring reading distance or gaze direction/by how much the head is lowered.

11. The method as claimed in claim 1, in which the messages emitted by the terminal in step e) comprise a request for the user to rotate his head about a horizontal axis and/or about a vertical axis and in which the processing of said at least one image or captured video sequence comprises detecting in the image a notable point of the ear of the user such as the tragion.

12. The method as claimed in claim 1, in which:
in step a) during the capture of at least one image or video sequence, the user is equipped with a spectacle frame;
the messages emitted by the terminal allow the user to be guided into at least one first posture in which the sagittal plane is aligned with the axis of the image capturing apparatus and at least one second posture in which the sagittal plane makes a nonzero angle to the axis of the image capturing apparatus; and
the images or video sequences are validated in these two postures.

13. The method as claimed in claim 1, comprising an additional step of selecting a language for the user from a plurality of languages, and in which, a set of validation and user guidance messages being recorded, each message is informationally tied to its audiovisual implementation in each of the languages of the plurality of languages, the message being delivered by the terminal to the user in correspondence with the instruction delivered by the remote-assistance center and in the language selected by the user.

14. The method as claimed in claim 1, in which step c) of processing, by the remote-assistance center, of said at least one image or video sequence transmitted in step b) and/or step d) of communicating, from the remote-assistance center to the electronic terminal of the user, said correction or validation instruction, is carried out by an automated system.

15. The method as claimed in claim 1, in which step c) of processing, by the remote-assistance center, of said at least one image or video sequence transmitted in step b) and/or step d) of communicating, from the remote-assistance center to the electronic terminal of the user, said correction or validation instruction, is carried out by an optician possessing a digital signature.

16. The method as claimed in claim 5, in which in step d), the audio-video remote-assistance comprises communicating to the user rescaling instructions including capturing at least one image of an element of known size, preferably placed in proximity to the eyes of the user, or capturing an image representative of the interpupillary distance of a user whose interpupillary distance is already known, or measuring a known reading distance in order to correct convergence, or even capturing an image of a frame having at least one predefined geometrical dimension.

17. The method as claimed in claim 5, in which step d) of audio-video remote-assistance comprises the following sub-steps:
a step in which the remote-assistance center transmits to the graphical interface of the terminal of the user a video stream or a known image; and
a step of capturing an image of the face or at least one eye of the user in response to this video stream or this known image.

18. The method as claimed in claim 5, in which step g) comprises verifying a value of a geometric adjustment parameter of a spectacle frame by comparing said determined value with a reference value.

19. The method as claimed in claim 5, in which step g) comprises measuring reading distance or gaze direction/by how much the head is lowered.

20. The method as claimed in claim 5, in which the messages emitted by the terminal in step e) comprise a request for the user to rotate his head about a horizontal axis and/or about a vertical axis and in which the processing of said at least one image or captured video sequence comprises detecting in the image a notable point of the ear of the user such as the tragion.

* * * * *